United States Patent [19]

Jensen et al.

[11] Patent Number: 5,424,430
[45] Date of Patent: Jun. 13, 1995

[54] DISUBSTITUTED POLYCYCLIC SYSTEMS AND PREPARATIVE METHODS THEREFOR

[75] Inventors: James H. Jensen; Timothy D. Costello; Leon De Brabander, Jr., all of Wilmington, Del.; Matthew E. Voss, Lincoln University, Pa.

[73] Assignee: The Du Pont Merck Pharmaceutical Company, Wilmington, Del.

[21] Appl. No.: 117,211

[22] Filed: Sep. 10, 1993

Related U.S. Application Data

[62] Division of Ser. No. 821,571, Jan. 16, 1992, Pat. No. 5,272,269.

[51] Int. Cl.⁶ .................. C07D 221/16; C07D 221/06
[52] U.S. Cl. .................... 546/111; 544/333; 544/405
[58] Field of Search ................ 546/111; 544/333, 405

[56] References Cited

U.S. PATENT DOCUMENTS 5,173,489 12/1992 Earl et al. ..................... 514/252

FOREIGN PATENT DOCUMENTS 311010 4/1989 European Pat. Off. .

OTHER PUBLICATIONS

Chemical Abstracts 96:51689w, 1982.

*Primary Examiner*—Alan L. Rotman
*Assistant Examiner*—D. Margaret M. Mach
*Attorney, Agent, or Firm*—Blair Q. Ferguson

[57] ABSTRACT

Polycyclic cognition enhancers having the general formula (1a), (1b) or (1c) are provided:

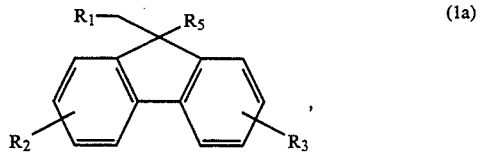

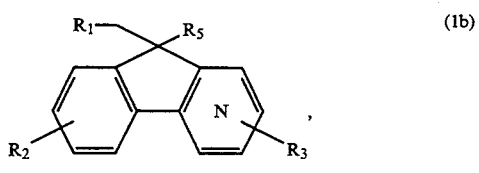

or

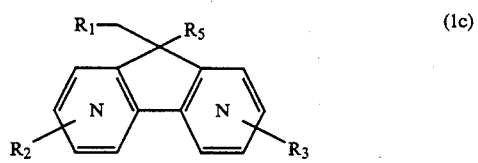

wherein:
$R_1$ is a heterocyclic aromatic moiety such as a 4-pyridyl, 2-pyridyl, 4-pyrimidyl, or pyrazinyl group;
$R_2$ and $R_3$ are independently H, F, Cl, Br, $NO_2$, $CONH_2$, $CON(R_4)(R_4')$, $S(O)_mR_4$, $CF_3$, or $N(R_4)(R_4')$;
$R_4$ and $R_4'$ are independently H, alkyl having from 1 to 4 carbon atoms, $CH_2$Phe—W, or Phe—W;
Phe is a phenyl group;
$R_5$ is —$(CH_2)_n$—Y or —$OCOR_4$;
Y is H, OH, $NH_2$, $NHR_4$, $N(R_4)(R_4')$, $NHCOR_4$, $NHCO_2R_4$, $NHS(O)_2R_4$, F, Cl, Br, $OR_4$, $S(O)_mR_4$, $CO_2H$, $CO_2R_4$, CN, $CON(R_4)(R_4')$, $CONHR_4$, $CONH_2$, $COR_4$, Phe, Phe—W, —C≡$CCO_2R_4$, —CH=$CHR_4$, —C≡$CR_4$, or a heterocyclic aromatic moiety such as a 4-pyridyl, 2-pyridyl, 4-pyrimidyl, or pyrazinyl group;
W is F, Cl, Br, $R_4$, $OR_4$, $NO_2$, $NH_2$, $NHR_4$, $N(R_4)(R_4')$, CN, or $S(O)_mR_4$;
m is 1 or 2; and
n is 1–7.

Also provided are preparative processes for these and other compounds.

17 Claims, No Drawings

DISUBSTITUTED POLYCYCLIC SYSTEMS AND PREPARATIVE METHODS THEREFOR

This is a division of application Ser. No. 07/821,571, filed Jan. 16, 1992, now U.S. Pat. No. 5,272,269.

FIELD OF THE INVENTION

This invention relates to disubstituted polycyclic compounds useful as cognition enhancers and, more particularly, to improved methods for the synthesis of such compounds.

BACKGROUND OF THE INVENTION

Increasingly there is a need for effective treatments for nervous system disorders and neurological deficiencies. Many of these diseases correlate with increasing age due mainly to degenerative changes in the nervous systems. Although in early stages of some diseases, certain systems are specifically affected (e.g., cholinergic systems in Alzheimer's Disease and Myasthenia Gravis, the dopaminergic system in Parkinson's Disease), multiple neurotransmitter system deficiencies (acetylcholine, dopamine, norepinephrine, serotonin) are generally found at later stages of disease such as senile dementia, multi-infarct dementia, Huntington's Disease, and mental retardation. This explains the generally observed multiple symptomatology that includes cognitive, neurological, and effective/psychotic components (See, e.g., Gottfries, *Psychopharmacol.*, 1985, 86, 245). Deficits in the synthesis and release of acetylcholine in the brain are generally thought to be related to cognitive impairment (See, e.g., Francis, et al., *New England J. Med.*, 1985, 7, 313) whereas neurological deficits (e.g. Parkinsonian symptoms) and mood/mental changes may be related to impairment of dopaminergic and serotonergic systems, respectively. Other neurological deficits (e.g. Myasthenia Gravis) are related to cholinergic deficiencies in the peripheral nervous system.

Treatment strategies employed previously encompass vasoactive drugs like vincamine and pentoxifylline; metabolic enhancers like ergoloid mesylates, piracetam, and naftidrofuryl; neurotransmitter precursors like 1-DOPA, choline, and 5-hydroxytryptamine; transmitter metabolizing enzyme inhibitors such as physostigmine; and neuropeptides like adrenocorticotropic hormone and vasopressin-related peptides. Except for 1-DOPA treatment for Parkinson's Disease and cholinesterase inhibitor treatment for Myasthenia Gravis, these treatment strategies have generally failed to enhance the residual function of the affected systems by enhancing the stimulus-induced release of neurotransmitters. Theoretically, such an enhancement would improve the signal-to noise ratio during chemical transmission of information, thereby reducing deficits in processes related to cognition, neurological function, and mood regulation.

It is known that certain polycyclic compounds enhance the stimulus-induced release of neurotransmitters, specifically acetylcholine in nervous tissues, and thus improve processes involved in learning and memorization of an active avoidance task. For example, European Patent Application 311,010, published Apr. 12, 1989, and U.S. Pat. No. 5,173,489 issued Dec. 22, 1992 discloses the utility as cognition enhancers of $\alpha,\alpha$-disubstituted aromatics or heteroaromatics having the formula:

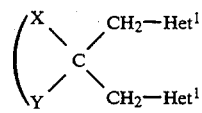

wherein X and Y are taken together to form a saturated or unsaturated carbocyclic or heterocyclic first ring and the shown carbon in said ring is $\alpha$ to at least one additional aromatic ring or heteroaromatic ring fused to the first ring, one of Het$^1$ or Het$^2$ is 2, 3, or 4-pyridyl; or 2, 4, or 5-pyrimidinyl, and the other is selected from:

(a) 2, 3, or 4-pyridyl
(b) 2, 4, or 5-pyrimidinyl
(c) 2-pyrazinyl
(d) 3 or 4-pyridazinyl,
(e) 3 or 4-pyrazolyl,
(f) 2 or 3 -tetrahydrofuranyl, and
(g) 3-thienyl.

SUMMARY OF THE INVENTION

The present invention provides polycyclic compounds of formula (1a), (1b), or (1c):

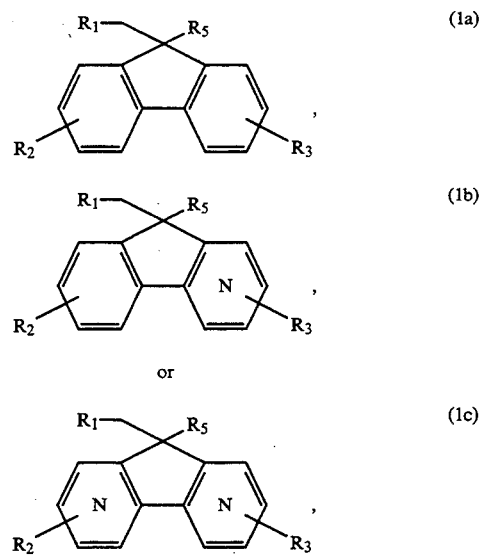

wherein:
$R_1$ is a heterocyclic aromatic moiety such as a 4-pyridyl, 2-pyridyl, 4-pyrimidyl, or pyrazinyl group;
$R_2$ and $R_3$ are independently H, F, Cl, Br, NO$_2$, CONH$_2$, CON(R$_4$)(R$_4$'), S(O)$_m$R$_4$, CF$_3$, or N(R$_4$)(R$_4$');
$R_4$ and $R_4$' are independently H, alkyl having from 1 to about 4 carbon atoms, CH$_2$Phe—W, or Phe—W;
Phe is a phenyl group;
$R_5$ is —(CH$_2$)$_n$—Y or —OCOR$_4$;
Y is H, OH, NH$_2$, NHR$_4$, N(R$_4$)(R$_4$'), NHCOR$_4$, NHCO$_2$R$_4$, NHS(O)$_2$R$_4$, F, Cl, Br, OR$_4$, S(O)$_m$R$_4$, CO$_2$H, CO$_2$R$_4$, CN, CON(R$_4$)(R$_4$'), CONHR$_4$, CONH$_2$, COR$_4$, Phe, Phe—W, —C≡CCO$_2$R$_4$, —CH═CHR$_4$, —C≡CR$_4$, or a heterocyclic aromatic moiety such as a 4-pyridyl, 2-pyridyl, 4-pyrimidyl, or pyrazinyl group;
W is F, Cl, Br, R$_4$, OR$_4$, NO$_2$, NH$_2$, NHR$_4$, N(R$_4$)(R$_4$'), CN, or S(O)$_m$R$_4$;
m is 1 or 2; and
n is 1–7.

The present invention further provides processes for preparing polycyclic compounds of the type shown by formula (1a), (1b) or (1c). In certain embodiments, the processes include, as a first step, reacting a ketone having formula (2a), (2b), or (2c) with a compound having the formula $R_1$—$CH_3$ in an acidic medium comprising a dehydrating agent to form an olefin having formula (4a), (4b) or (4c).

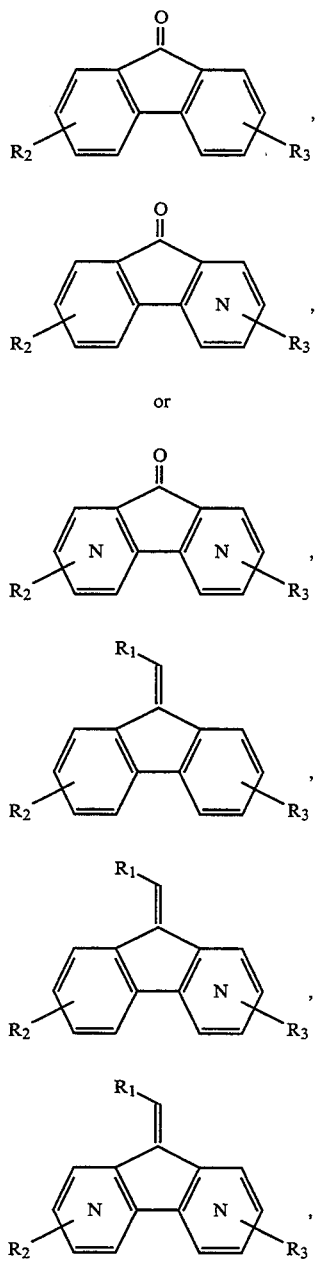

Aqueous base and, optimally, an oxidizing agent is then added to isolate the olefin. The olefin is reduced to produce a compound having formula (5a), (5b) or (5c), which is reacted with a compound having formula $R_5$—L, wherein L is a leaving group, to form a di-substituted compound having formula (1a), (1b) or (1c).

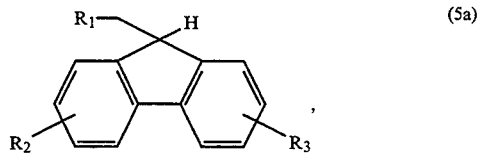

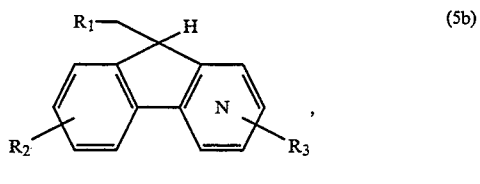

or

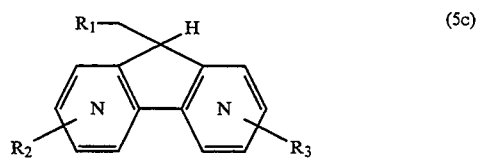

DETAILED DESCRIPTION OF THE INVENTION

The polycyclic compounds of this invention are generally synthesized by reacting a fluorenone, azafluorenone or diazafluoreneone of formula (2a), (2b) or (2c) with a compound having formula $R_1$—$CH_3$ in an acidic medium containing a dehydrating agent to form an olefin having formula (4a), (4b) or (4c). It is believed that this reaction proceeds through dehydration of a carbinol having formula (3a), (3b) or (3c).

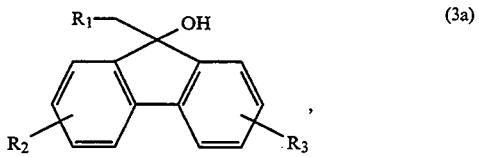

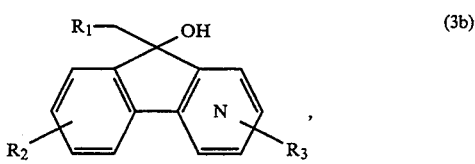

or

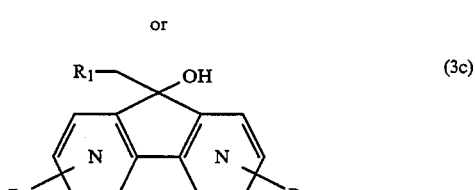

$R_1$ can be any of a wide variety of heterocyclic aromatic moieties, preferably a 2-pyridyl, 4-pyrimidyl, or pyrazinyl group, more preferably a 4-pyridyl group. Where a compound of formula (2a) is employed, $R_2$ and $R_3$ preferably are both electron withdrawing groups. Preferred reaction mediums comprise aliphatic acids having 1 to about 7 carbon atoms; acetic acid is particularly preferred. Dehydrating agents that can be used in the reaction medium according to the invention include aliphatic acid chlorides having 1 to about 7 carbon atoms, acid anhydrides having the formula $R_a$—C(O)—O—C(O)—$R_b$ wherein $R_a$ and $R_b$ are alkyl having from 1 to about 7 carbon atoms, and combinations thereof. A preferred dehydrating agent is acetic anhydride.

Aqueous base is then added to the acidic reaction mixture to isolate the olefin having formula (4a), (4b) or (4c). Preferably the aqueous base comprises potassium hydroxide, sodium hydroxide, calcium hydroxide, or combinations thereof; sodium hydroxide is particularly preferred. In certain preferred embodiments, an oxidizing agent is added along with the aqueous base to improve the handling, appearance, and yield of the olefinic product. Representative oxidizing agents include hypochlorites having the formula MOCl wherein M is a metal cation. Sodium hypochlorite is a preferred oxidizing agent. The oxidizing agent should be added in an amount and under conditions that will not oxidize the olefin to its corresponding ketone.

The olefin of formula (4a), (4b) or (4c) is then reduced, typically with sodium borohydride or with hydrogen gas and a suitable catalyst in a suitable solvent. Preferred solvents include alkyl alcohols having from 1 to about 5 carbon atoms, more preferably methanol or ethanol. Catalytic reductions using, for example, palladium-on-carbon have been found to provide a purer product in high yield. A minor impurity formed in certain instances can be suppressed by the addition of a base which is insoluble in the solvent employed in the reduction. Useful alcohol-insoluble bases include magnesium oxide, calcium oxide, sodium carbonate, sodium bicarbonate, or combinations thereof.

The reduction product thus formed, designated by formula (5a), (5b) or (5c), is treated with base in protic or aprotic solvent to generate an anionic specie, which is alkylated with a compound having formula $R_5$—L. $R_5$ can be —$(CH_2)_n$—Y or —$OCOR_4$ where Y is H, OH, $NH_2$, $NHR_4$, $N(R_4)(R_4')$, $NHCOR_4$, $NHCO_2R_4$, $NHS(O)_2R_4$, F, Cl, Br, $OR_4$, $S(O)_mR_4$, $CO_2H$, $CO_2R_4$, CN, $CON(R_4)(R_4')$, $CONHR_4$, $CONH_2$, $COR_4$, Phe, Phe—W, —C≡$CCO_2R_4$, —CH=$CHR_4$, —C≡$CR_4$, or a heterocyclic aromatic moiety such as a 4-pyridyl, 2-pyridyl, 4-pyrimidyl, or pyrazinyl group. Preferably, $R_5$ is —$CH_2$—(4-pyridyl). L can be any of the leaving groups known in the art, including halides and sulfonates. Preferably, L is chloride. Suitable bases for forming the anion include but are not limited to alkoxides having from 1 to about 7 carbon atoms. A preferred base is tert-butoxide formed by reaction of sodium hydroxide with tert-butanol in water.

Additional objects, advantages, and novel features of this invention will become apparent to those skilled in the art upon examination of the following examples thereof, which are not intended to be limiting.

EXAMPLE 1

A reactor was constructed consisting of a 22 liter round bottom flask equipped with a mechanical agitator, condenser, thermocouple with controller, heating mantle, nitrogen blanket, and charging funnel. An addition funnel was used for charging NaOH and a peristaltic pump with a timer was used to charge NaOCl. Vacuum filter flasks and ceramic funnels with Dacron ® sail cloth were used for all filtrations. Appropriate ground glass stoppers were used as needed. All equipment was cleaned and inspected before use.

1a. Synthesis of 5-(4-Pyridinylmethylene)-5H-cyclopenta[2,1-b:3,4-b']-dipyridine (Formula (6))

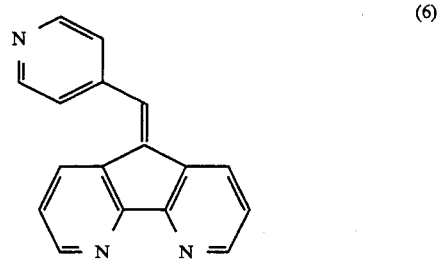

(6)

Approximately 700 grams of 4,5-diazafluoren-9-one, acetic anhydride (800 grams, 2.0 moles per mole fluorenone), and 4-picoline (1430.8 grams, 4.0 moles per mole fluorenone) were charged to the reactor. The fluorenone was prepared according to the patent application entitled "Polycyclic Ketones and Preparative Methods Therefor", filed herewith, in the name of Crapps, et al. A total of 1680 grams acetic acid (2.4 grams per gram fluorenone) was charged and used as a rinse. The reaction mixture was heated to 120° C. with a heating mantle. Heating was maintained at 120° C. for approximately 8 hours. Samples were taken every hour for liquid chromatographic analysis. The reaction was continued until the fluorenone was reduced to less than 2 area percent. Water (11.2 kilograms, 16 ml per gram of fluorenone) was added and the reaction mixture was allowed to cool to 50°–80° C.

A 50% solution of NaOH (455 ml, 0.65 ml per gram of fluorenone) was then charged to the addition funnel and used to neutralize the reaction mixture to pH 4.8–5.0. A temperature of 65° C. or less was maintained during the neutralization by adjusting the rate of addition and by immersing the reaction mixture in an ice water bath.

The reaction mixture was then cooled slowly to 25°–30° C. and 788 ml of 4.0% NaOCl was added. Maintaining the temperature of the reaction mixture below 30° C., the NaOCl was added over about 4 hours. The pH of the reaction mixture was adjusted to 6.7 by addition of 50% NaOH. The reaction mixture was then cooled to 0°–5° C. with ice and held in that range for two hours. The formed precipitate was filtered using large ceramic funnels and sail cloth. The filter cake was packed and washed with water (2×800 ml). The precipitate was analyzed for the target compound by liquid chromatography.

Three batches of the target olefin were combined and recrystallized by charging the combined material (2000 grams of active ingredient) to the reactor along with 12.2 kilograms water and 4000 ml acetonitrile. The solution was heated to reflux (about 80° C.) and held for 30 minutes. The solution was then cooled slowly to 30° C. and 250 ml 4.0% NaOCl added over a period of 4 hours. The reaction mixture was allowed to stir overnight, after which it was cooled to 0°–5° C. and filtered using large ceramic funnels and sail cloth. The precipitate was then washed with water and dried at ambient temperatures. The dried olefin was recrystallized a second time and dried to a constant weight in a vacuum oven at 50°–70° C. with a nitrogen sweep. The analytical purity of the olefin was determined by liquid chromatography.

1b. Synthesis of 9-(4-Pyridinylmethyl)-9H-cyclopenta[2,1-b:3,4-b']-dipyridine (Formula (7))

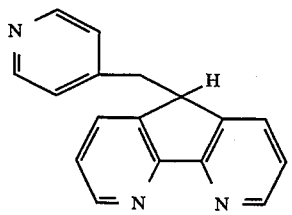
(7)

(i) Trial 1

Olefin having formula (6) (50 grams) was hydrogenated at about 15–20 psig with hydrogen gas in an autoclave over 11 grams of 5% palladium-on-carbon (0.22 g per gram of olefin) in absolute ethanol (370 ml, 7.5 ml per gram of olefin). The ethanolic solution was placed in an approximately 500 ml flask and warmed to reflux. The carbon and catalyst were removed by passing the hot suspension through GF/B glass fiber filter paper, which removed particles greater than 1 μm. The carbon was rinsed with 200 ml of warmed, fresh ethanol and the filtrate was charged to a 2.0 liter round bottomed flask equipped with a takeoff condenser. An addition funnel was charged with water (450 ml, 9 ml per gram of olefin). The reaction mixture was heated and ethanol distilled and replaced with an approximately equal volume of water. The distillation was maintained until the head temperature reached 95°–96° C. and 105% of the original volume had been displaced. The heating mantle was then removed and the mixture allowed to cool slowly to room temperature (25°–30° C.). Upon reaching this temperature, a wet ice/acetone bath was placed around the flask and the reaction mixture cooled to 0°–5° C. This temperature was maintained for 2 hours.

The formed solids were then collected by vacuum filtration through the sail cloth. The filter cake was washed with fresh water (300 ml; approximately 2 ml per gram of solid). The solids were dried overnight in the vacuum oven at 50° C. with a nitrogen bleed.

The solids were then charged to an approximately 500 ml round bottomed flask fitted with a reflux condenser, along with 350 ml of a premixed 10% ethanol/water (v/v) solution (7 ml per gram of solid). The mixture was heated to reflux until the solids dissolved; a slight cloud to the solution remained. The heat was removed and the solution was allowed to cool to 25°–30° C. then to 0°–5° C. and maintained at this temperature for 30 minutes. The formed solids were collected by vacuum filtration on the sail cloth and the filter cake washed with 200 ml fresh water. The solids were dried to constant weight in a vacuum oven at 50° C. with a nitrogen bleed. Compound having formula (7) was recovered in 94.7% yield.

(ii) Trial 2

Olefin having formula (6) (12 grams) was combined with 70 ml methanol in a 250 ml 3-necked round bottomed flask fitted with a reflux condenser, magnetic stirring bar, and nitrogen flush. The mixture was stirred and cooled below 5° C. Solid sodium borohydride (0.5 grams) was then added over the course of 30 minutes. An additional 5 ml portion of methanol was used to rinse the sodium borohydride clinging to the sides of the flask. The mixture turned into a transparent brown solution after approximately 0.5 hour. Thin layer chromatography of the reaction solution versus a sample of starting material (silica plate developed in 90/10 (v/v) methanol/water) indicated that the starting material had been consumed. The crude reaction was transferred to a 125 ml addition funnel, added dropwise to 210 ml of water, and cooled to 0° C. This precipitated a solid that was isolated by filtration and dried in a 50° C. vacuum oven to yield 10 grams (83%) of a purplish solid having formula (7).

EXAMPLE 2

Synthesis of 9,9-Bis(4-pyridinylmethyl)-5H-cyclopenta[2,1b:3,4-b']-dipyridine (Formula (8))

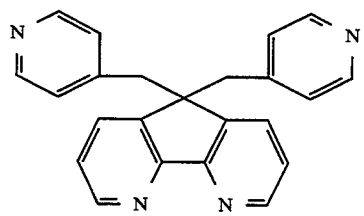
(8)

(i) Trial 1

Compound having formula (7) (304 g) and isopropanol (600 ml; 4.0 ml per gram of (7)) were charged to a 5 liter round bottomed flask equipped with a mechanical stirrer, thermometer, 2 liter addition funnel, nitrogen inlet, and a powder funnel. Any loose (7) was rinsed into the flask with 600 ml more isopropanol. The slurry was stirred and cooled to <5° C. with an ice bath. The powder funnel was then replaced with a 250 ml addition funnel, which was charged with 225 ml of 50% NaOH (0.75 ml per gram of (7)). The NaOH solution was added at a rate that kept the temperature of the slurry below 10° C.

A 2 liter addition funnel was then charged with a solution made by dissolving 212 g of 4-picolyl chloride hydrochloride (0.7 g per gram of (7)) in 1 liter of water (5 ml per gram of 4-picolyl chloride hydrochloride). This solution was added to the stirring mixture, again keeping the temperature of the contents of the flask below 10° C. After this addition was complete, the ice bath was removed and the stirring mixture warmed passively to ambient temperature. The disappearance of compound having formula (7) and the appearance compound having formula (8) was monitored by high performance liquid chromatography.

The reaction mixture was then transferred to a 22 liter flask cooled in an ice bath. Using a 4 liter addition funnel, 5.0 liters of water was added dropwise over 0.5 hours. After the addition was complete, the mixture was left stirring in the ice bath for 3 hours. The precipitated solids were removed by vacuum filtration. The filter cake was washed with fresh water and dried overnight in a room temperature vacuum oven with a nitrogen purge.

Two further batches were prepared and the combined solids from all three runs were charged to a 12 liter round bottomed flask with 1500 ml of absolute ethanol, then 3500 ml of water. The mixture was heated to reflux (87° C.) until solids dissolved into a red-brown solution and held at reflux for 15 minutes. Heating was discontinued and the mixture was allowed to cool to ambient temperature overnight.

The flask was then cooled in an ice bath to <5° C. and held at that temperature for 3 hours. The formed yellow solids were collected by vacuum filtration and dried in a room temperature vacuum oven over a weekend. The solids were recrystallized a second time with 1080 ml of ethanol and 2520 ml of water. The target compound was recovered in 82.3% yield after 2 recrystallizations.

(ii) Trial 2

Compound having formula (7) (523 grams), tert-butanol (1.5 liters), and water (780 ml) were combined in a 12.0 liter 3-necked round bottomed flask equipped with a mechanical stirrer, reflux condenser, and a 2.0 liter addition funnel. The mixture was stirred and cooled below 9° C. with an ice bath. Over the next 45 minutes 392 ml of 50% aqueous sodium hydroxide was added dropwise through the addition funnel. The temperature was maintained below 15° C. throughout the addition. A separate solution made from 2.6 liters water and 366 grams 4-picolyl chloride hydrochloride was then added through the addition funnel over the course of 2.0 hours, maintaining the temperature below 15° C. The ice bath was removed and the stirring mixture allowed to warm to ambient temperature. The consumption of (7), measured by HPLC, was complete after about 5 hours.

The product was isolated by slowly adding 4.2 liters of water to the stirring reaction mixture and cooling the reaction mass below 6° C. with an ice bath. The solids were isolated by filtration on sail cloth and washed with three 1000 ml portions of fresh water. The solids were allowed to dry at room temperature under a dry nitrogen stream to provide approximately 606 grams (86%) of crude product, which was recrystallized as in Example 2(i).

Those skilled in the art will appreciate that numerous changes and modifications can be made to the preferred embodiments of the invention and that such changes and modifications can be made without departing from the spirit of the invention. For example, the syntheses set forth in Examples 1 and 2 can be readily adapted through relatively minor modifications to the preparation of the full range of compounds represented by formula (1a), (1b) or (1c). It is therefore intended that the appended claims cover all such equivalent variations as fall within the true spirit and scope of the invention.

What is claimed is:

1. A process for preparing an olefin having a formula:

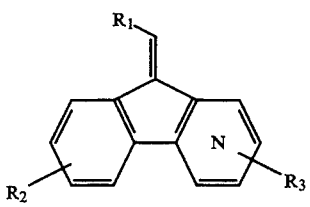

wherein:
$R_1$ is a 4-pyridyl, 2-pyridyl, 4-pyrimidyl, or pyrazinyl group;
$R_2$ and $R_3$ are independently H, F, Cl, Br, $NO_2$, $CONH_2$, $CON(R_4)(R_4')$, $S(O)_mR_4$, $CF_3$, or $N(R_4)(R_4')$;
$R_4$ and $R_4'$ are independently H, alkyl having from 1 to 4 carbon atoms, $CH_2Phe-W$, or Phe—W;
Phe is a phenyl group;
W is F, Cl, Br, $NO_2$, $NH_2$, CN, H, alkyl having from 1 to 4 carbon atoms, or OH; and
m is 1 or 2;
comprising the steps of:
providing a first compound having a formula:

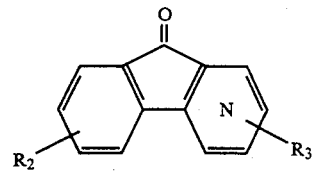

providing a second compound having the formula $R_1$—$CH_3$ wherein $R_1$ is a 4-pyridyl, 2-pyridyl, 4-pyrimidyl, or pyrazinyl group; and
contacting said first compound and said second compound in an acidic medium comprising dehydrating agent to form an acidic reaction mixture comprising said olefin.

2. The process of claim 1 wherein said second compound is a 4-picoline.

3. The process of claim 1 wherein said acidic medium comprises an aliphatic acid having 1 to about 7 carbon atoms.

4. The process of claim 1 wherein said acidic medium comprises acetic acid.

5. The process of claim 1 wherein said dehydrating agent comprises an aliphatic acid chloride having 1 to about 7 carbon atoms, acid anhydrides having the formula $R_a$—C(O)—O—C(O)—$R_b$ wherein $R_a$ and $R_b$ are alkyl having from 1 to 7 carbon atoms, or combinations thereof.

6. The process of claim 1 wherein said dehydrating agent is acetic anhydride.

7. The process of claim 1 further comprising contacting said acidic reaction mixture with base to isolate said olefin.

8. The process of claim 7 wherein said base is sodium hydroxide.

9. The process of claim 7 wherein said contacting of said acidic reaction mixture and said base is performed in the presence of oxidizing agent.

10. The process of claim 9 wherein said oxidizing agent comprises a hypochlorite having the formula MOCl wherein M is a metal cation.

11. The process of claim 9 wherein said oxidizing agent comprises sodium hypochlorite.

12. A compound having a formula:

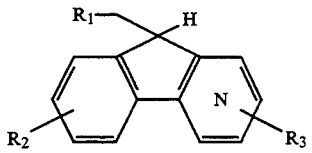

wherein:
$R_1$ is a 4-pyridyl, 2-pyridyl, 4-pyrimidyl, or pyrazinyl group;
$R_2$ and $R_3$ are independently H, F, Cl, Br, $NO_2$, $CONH_2$, $CON(R_4)(R_4')$, $S(O)_mR_4$, $CF_3$, or $N(R_4)(R_4')$;
$R_4$ and $R_4'$ are independently H, alkyl having from 1 to 4 carbon atoms, $CH_2Phe-W$, or Phe—W;
Phe is a phenyl group;

W is F, Cl, Br, $NO_2$, $NH_2$, CN, H, alkyl having from 1 to 4 carbon atoms, or OH; and m is 1 or 2.

13. A process for preparing a di-substituted compound having a formula:

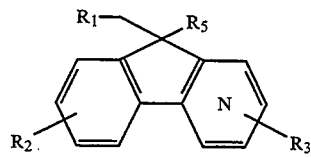

wherein:

$R_1$ is a 4-pyridyl, 2-pyridyl, 4-pyrimidyl, or pyrazinyl group;

$R_2$ and $R_3$ are independently H, F, Cl, Br, $NO_2$, $CONH_2$, $CON(R_4)(R_4')$, $S(O)_mR_4$, $CF_3$, or $N(R_4)(R_4')$;

$R_4$ and $R_4'$ are independently H, alkyl having from 1 to 4 carbon atoms, $CH_2Phe$—W, or Phe—W;

Phe is a phenyl group;

$R_5$ is —$(CH_2)_n$—Y or —$OCOR_4$;

Y is H, OH, $NH_2$, $NHR_4$, $N(R_4)(R_4')$, $NHCOR_4$, $NHCO_2R_4$, $NHS(O)_2R_4$, F, Cl, Br, $OR_4$, $S(O)_mR_4$, $CO_2H$, $CO_2R_4$, CN, $CON(R_4)(R_4')$, $CONHR_4$, $CONH_2$, $COR_4$, Phe, Phe—W, —$C\equiv CCO_2R_4$, —$CH=CHR_4$, —$C\equiv CR_4$, or a 4-pyridyl, 2-pyridyl, 4-pyrimidyl, or pyrazinyl group;

W is F, Cl, Br, $NO_2$, $NH_2$, CN, H, alkyl having from 1 to 4 carbon atoms, or OH; and m is 1 or 2; and n is 1–7;

comprising the steps of:

providing a first, mono-substituted compound having a formula:

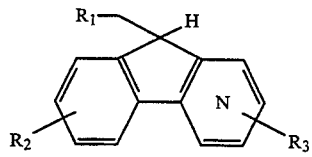

providing a second compound having the formula $R_5$—L, wherein L is a leaving group; and contacting said first compound and said second compound in the presence of base to form said di-substituted compound.

14. The process of claim 13 wherein L is Cl, Br, or I.

15. The process of claim 13 wherein said second compound is 4-picolyl chloride hydrochloride.

16. The process of claim 13 wherein said base comprises an alkoxide having from 1 to 7 carbon atoms.

17. The process of claim 13 wherein said base comprises tert-butoxide anion.

* * * * *